(12) United States Patent
Shin (10) Patent No.: US 9,339,455 B2
(45) Date of Patent: May 17, 2016

(54) NATURAL ANTI-BACTERIAL TOOTHPASTE COMPOSITION CONTAINING IMPROVEMENT IN TOOTH PAIN, ANTIBACTERIAL MOUTH AND NERVE STABILITY

(71) Applicant: Dong-Mock Shin, Goyang-si (KR)

(72) Inventor: Dong-Mock Shin, Goyang-si (KR)

( * ) Notice: Subject to any disclaimer, the term of this patent is extended or adjusted under 35 U.S.C. 154(b) by 0 days.

(21) Appl. No.: 14/376,518

(22) PCT Filed: Mar. 6, 2013

(86) PCT No.: PCT/KR2013/001797
§ 371 (c)(1),
(2) Date: Aug. 4, 2014

(87) PCT Pub. No.: WO2013/141500
PCT Pub. Date: Sep. 26, 2013

(65) Prior Publication Data
US 2015/0023891 A1    Jan. 22, 2015

(30) Foreign Application Priority Data

Mar. 22, 2012 (KR) ........................ 10-2012-0029219

(51) Int. Cl.
| | | |
|---|---|---|
| *A61Q 11/00* | (2006.01) |
| *A61K 8/24* | (2006.01) |
| *A61K 8/25* | (2006.01) |
| *A61K 8/97* | (2006.01) |
| *A61Q 17/00* | (2006.01) |
| *A61K 33/00* | (2006.01) |
| *A61K 33/06* | (2006.01) |
| *A61K 33/26* | (2006.01) |
| *A61K 9/00* | (2006.01) |
| *A61K 8/34* | (2006.01) |
| *A61K 8/73* | (2006.01) |

(52) U.S. Cl.
CPC ... *A61K 8/97* (2013.01); *A61K 8/24* (2013.01); *A61K 8/25* (2013.01); *A61K 8/34* (2013.01); *A61K 8/345* (2013.01); *A61K 8/732* (2013.01); *A61K 9/0053* (2013.01); *A61K 33/00* (2013.01); *A61K 33/06* (2013.01); *A61K 33/26* (2013.01); *A61Q 11/00* (2013.01); *A61Q 17/005* (2013.01); *A61K 2800/5922* (2013.01); *A61K 2800/70* (2013.01)

(58) Field of Classification Search
USPC ............................................. 424/49, 57, 58
See application file for complete search history.

(56) References Cited

U.S. PATENT DOCUMENTS 7,182,937 B2    2/2007    Xu et al.

FOREIGN PATENT DOCUMENTS

| JP | 10-500993 A | 1/1998 |
| KR | 10-2004-0043397 A | 5/2004 |
| KR | 10-2008-0013445 A | 2/2008 |
| KR | 10-0815397 B1 | 3/2008 |

*Primary Examiner* — Lezah Roberts
(74) *Attorney, Agent, or Firm* — Novick, Kim & Lee, PLLC; Jae Youn Kim (57) ABSTRACT

The present invention relates to natural anti-bacterial toothpaste composition containing improvement in tooth pain, antibacterial mouth and nerve stability and particularly, it enables to contribute to improvement in tooth pain, antibacterial mouth and nerve stability, which represent effects of $Na_2SiO_3\text{-}10H_2O$ and oriental medicine, due to more than 63~75% of $SiO_3$, and $Na_2SiO_3\text{-}10H_2O$ and oriental medicine containing natural minerals like calcium, iron, magnesium, etc.

1 Claim, 11 Drawing Sheets

NATURAL ANTI-BACTERIAL TOOTHPASTE COMPOSITION CONTAINING IMPROVEMENT IN TOOTH PAIN, ANTIBACTERIAL MOUTH AND NERVE STABILITY

TECHNICAL FIELD

The present invention relates to toothpaste composition, and more particularly, to natural anti-bacterial toothpaste composition containing improvement in tooth pain, antibacterial mouth and nerve stability due to $Na_2SiO_3$-$10H_2O$ and oriental medicine.

BACKGROUND ART

Used to brush tooth surfaces, toothpastes belong to drug medicine causing minor effects to human beings. Particularly, toothpastes are mainly used for whitening effects, bactericidal effects, interdental cleaning effects, etc. For this, toothpastes generally comprise components such as abrasives, humectants, forming agents and flavoring agents.

Halitosis occurs when unpleasant odors are exhaled in breathing. It is caused by acquired systemic diseases, or smelly substances, wherein amino enzyme breaks down amino acids from which proteins, food wastes, etc. in saliva are disassembled and generated by microorganisms in a mouth. That is, halitosis may be caused by local factors in a mouth like dental caries or periodontitis, or by physical diseases in a mouth like diabetes, liver disease, etc. However, even healthy people may have halitosis because of food wastes or germs which remain in a mouth, and especially, it often happens to the people in middle age or old people and gets worse in the morning. Particularly, Koreans prefer foods with strong smell such as garlic or Kimchi, thereby having foul breath in a mouth. Therefore, studies on effective reduction method have been actively in progress.

Further, periodontal disease is deposited by various kinds of germs and microorganisms, thereby causing gingival inflammation, bleeding, periodontal pocket formation and alveolar bone destruction and finally damaging teeth. The causes of the periodontal disease are bacteria, combined to sugar in food and strongly adhered to teeth like moss, and dental calculus, which calcifies toxic dental plaque of metabolite of the bacteria. Generally, periodontal disease has no symptoms and toothache except bleeding gums or bad breath in a mouth at times and thus, most people fails to show noticeable symptoms even though they have periodontitis. When people feel uncomfortable, it is normally hard to have dental treatment because of damaged periodontal tissue. Also, if periodontal disease begins, alveolar bones surrounding dental roots are widely destructive, and most of teeth become useless. Therefore, since damaged periodontal tissue has limited regenerative capability, it is mostly impossible to restore teeth back to their original healthy state even after treatment.

Furthermore, dentin hypersensitivity (symptoms of sensitive teeth, etc) is sensation felt when the dentin of the exposed teeth approaches to cold air or stimulated food, etc. The sensation can range from minor symptoms all the way to intense, persistent pain.

Symptoms variously appear according to the degrees of exposed dentinal tubules. A tooth consists of dental enamel over the surface of the tooth, dentin right below the dental enamel, dental pulp in nerves and blood vessels, and gum tissue protecting the tooth. However, if wrong toothbrushing, gum disease and dental caries make dental enamel damaged, or dentin is exposed by gum sinking, external stimuli are transferred to dental nerves through dentinal tubules in dentin, thereby causing short, sharp pain. Especially, the young have dentin hypersensitivity more and more these days and thus, it needs to have dental treatment in early stage.

In addition, for preventing dental caries, 0.05~0.1 w/v % concentration of fluorine is often used in toothpastes or mouthwash. However, according to recent reports, fluorine compounds in toothpastes or mouthwash may prevent dental caries, but it is revealed that constant and repetitive use of fluorine compounds stimulates gum infection.

Therefore, toothpaste composition which may prevent dentin hypersensitivity and dental caries without fluorine has been demanded.

In accordance with such request, Korean Patent Registration nos. 10-0806050 and 10-0815397 and Korean Patent Publication no. 10-2008-0013445 have disclosed toothpaste composition whose main component is powder-shaped sodium silicate, 1.0~2.5 μm diameter, for the total weight of toothpaste composition.

When the sodium silicate dissolves, water-soluable silicate is compounded of water, body fluid, or blood composition and responds in various forms such as $Na_2SiO_3$-$5H_2O$, $Na_2SiO_3$-$7H_2O$, ..., $Na_2SiO_3$-$9H_2O$, $Na_2SiO_3$-$10H_2O$, ..., $Na_2SiO_3$-$15H_2O$, $Na_2SiO_3$-$16H_2O$. However, it is the problem that these belong to inappropriate food additives except $Na_2SiO_3$-$9H_2O$, $Na_2SiO_3$-$10H_2O$, approved as food additives by U.S. Food and Drug Administration.

DETAILED EXPLANATIONS OF THE INVENTION

Technical Problem

For solving above problems, the object of the present invention is to provide natural anti-bacterial toothpaste composition containing improvement in tooth pain, antibacterial mouth and nerve stability by means of $Na_2SiO_3$-$10H_2O$, a main material.

Further, the other object of the present invention is to provide natural anti-bacterial toothpaste composition containing improvement in tooth pain, antibacterial mouth and nerve stability due to oriental medicine contained in toothpaste composition.

Technical Solution

To accomplish above objects, the present invention is characterized by comprising $Na_2SiO_3$-$10H_2O$ in toothpaste composition.

Here, the total weight of the toothpaste composition is made up of 24~55% of $Na_2SiO_3$-$10H_2O$, 12~25% of powder-shaped silicon dioxide, 14~17% of liquid D-sorbitol, 8~12% of powder-shaped corn starch, 4~5% of liquid concentrated glycerin, 2~3% of liquid *Glycyrrhiza uralensis* Fischer, 1~2% of liquid Chinese pepper, 0.4~2% of liquid green tea extracts, 0.6~1% of liquid *angelica gigas* Nakai, 0.4~1% of liquid *rehmannia glutinosa* var. *purpurea*, 0.4~1% of liquid *Sophora flavescens* Alton, 0.4~1% of liquid *Platycodon grandiflorum* A. De Candolle, 0.4~1% of liquid *Prunus mume* Slebold et Zuccarini, 0.4~1% of powder-shaped calcium hydrogen phosphate dehydrate, 0.2~2% of liquid peppermint oil and 0.2~2% of liquid DL-menthol.

Advantageous Effects

According to natural anti-bacterial toothpaste composition containing improvement in tooth pain, antibacterial mouth and nerve stability of the present invention, as constituted above, it enables to contribute to improvement in tooth pain, antibacterial mouth and nerve stability, which represent effects of $Na_2SiO_3$-$10H_2O$ and oriental medicine containing water-soluable natural minerals like water-soluable calcium, water-soluable iron, water-soluable magnesium, etc. due to more than 63% of $SiO_3$.

Further, the present invention enables to remove causes of dental plaque by completely fighting 8 types of dental bacteria as antibacterial effects of reduction of germs in a mouth; to prevent dental abrasion at most due to liquid abrasives containing inverted triangle shaped $SiO_3$ molecule; and to coat tooth surfaces for more than 7 hours simultaneously with protecting teeth and dentine and preventing a toothache by sealing dental tubules.

Furthermore, the present invention enables to cure a toothache by sealing dental tubules semipermanently; to soften a mouth, easily vulnerable to hurt, by means of toothpastes which have no surfactants, fluorides, preservatives and saccharin; to be safely available for the old, whose mucous membranes of oral cavities are getting thin along with xerostomia, thereby sensitive to minor stimulation as they grow older, critically ill patients, diabetic patients, cancer patients, people who have dental implants, artificial teeth and dental prosthesis, and pregnant women and kids; and not to alter taste perception after toothbrushing due to toothpastes which have no surfactants, fluoride, preservatives and saccharin.

DESCRIPTION OF THE PREFERRED EMBODIMENTS

The configuration of natural anti-bacterial toothpaste composition containing improvement in tooth pain, antibacterial mouth and nerve stability, according to the present invention, will be described in detail with the accompanying drawing.

In the following description of the present invention, a detailed description of known incorporated functions and configurations will be omitted when to include them would make the subject matter of the present invention rather unclear. Also, the terms used in the following description are defined taking into consideration the functions provided in the present invention. The definitions of these terms should be determined based on the whole content of this specification, because they may be changed in accordance with the option of a user or operator or a usual practice.

The total weight of the toothpaste composition according to the present invention is made up of 24~55% of $Na_2SiO_3$-$10H_2O$, 12~25% of powder-shaped silicon dioxide, 14~17% of liquid D-sorbitol, 8~12% of powder-shaped corn starch, 4~5% of liquid concentrated glycerin, 2~3% of liquid *Glycyrrhiza uralensis* Fischer, 1~2% of liquid Chinese pepper, 0.4~2% of liquid green tea extracts, 0.6~1% of liquid *angelica gigas* Nakai, 0.4~1% of liquid *rehmannia glutinosa* var. *purpurea*, 0.4~1% of liquid *Sophora flavescens* Alton, 0.4~1% of liquid *Platycodon grandiflorum* A. De Candolle, 0.4~1% of liquid *Prunus mume* Slebold et Zuccarini, 0.4~1% of powder-shaped calcium hydrogen phosphate dehydrate, 0.2~2% of liquid peppermint oil and 0.2~2% of liquid DL-menthol. Preferably, the total weight of the toothpaste composition according to the present invention is made up of 45% of $Na_2SiO_3$-$10H_2O$, 15% of silicon dioxide, 15% of D-sorbitol, 10% of corn starch, 4.5% of concentrated glycerin, 2.5% of *Glycyrrhiza uralensis* Fischer, 1.2% of green tea extracts, 1.2% of Chinese pepper, 0.9% of *angelica gigas* Nakai, 0.8% of *rehmannia glutinosa* var. *purpurea*, 0.6% of *Sophora flavescens* Alton, 0.6% of *Platycodon grandiflorum* A. De Candolle, 0.6% of *Prunus mume* Slebold et Zuccarini, 0.6% of calcium hydrogen phosphate dehydrate, 0.8% of peppermint oil and 0.8% of DL-menthol.

$Na_2SiO_3$-$10H_2O$ is a new substance, called as UMO, referring to water-soluable complex minerals produced by strengthening and upgrading functions of UMO, as an existing food additive, which is allowed to be produced for food additives and drinking water additives in accordance with toothpastes. This refers to a substance in which silicon (Si, 99%), a main component of silica stone, a natural mineral, is melted at high temperatures, changed to crystal figure and then, dissolves in water again. Based on this, the toothpaste composition of the present invention contains Si, Ca, Na, Ma, Fe, etc., which are improved for strongly fighting all dental germs in teeth, gums, etc., and especially, more than 75% of $SiO_3$ in $Na_2SiO_3$-$10H_2O$.

$Na_2SiO_3$-$10H_2O$ meets requirement of Article 18(2) of Korean Water Quality Management Act and has cellular activities, permeability, germicidal power, anti-inflammation, purification and nerve stability due to more than 63% of $SiO_3$ and natural minerals such as calcium, iron, natrium, magnesium, etc.

One of five major nutrients which are proteins, fats, carbohydrates and vitamins constituting a living body, water-soluable minerals help immunize body through appropriately maintaining alkalescent pH of 7.35-7.45 for working human organism, blood, cells, etc. normally; detoxicate all sorts of external toxins like active oxygen, metal, exhaust gas, endocrine-disrupting chemicals, etc. generated from body; maintain normal acidity or basicity, which is necessary for metabolic responses; control water balance in the body; and act as a catalyst in several physical responses.

Mainly constituted of blood vessels, bones and hair, water-soluable silicon supplements inner strength and patience. Silicon is a necessary mineral for mind while the rest of minerals except silicon are important for body. It exists in brown rice or barley, especially in fiber waste. Thus, it is easy for modern people who mostly eat pure white food to lack silicon. A lack of silicon generates aging, memory impairment, lack of patience, incurable bone disease, etc.

As a mineral which prevents acidification of body fluids, water-soluable calcium is the most essential component for life support, activating insulin secretion and strengthening adaptability towards stress with stabilizing nerves and mind. It is the second largest after carbon, hydrogen and oxygen among body components. Approximately 1% of calcium is the one with protein and the other with ionic composition of body fluids. Particularly, water-soluable calcium helps formation of bones and teeth, blood coagulation, and absorption of vitamin A, C, D and P, thereby getting involved in production of oxygen and mother's milk. Thus, it is the essential mineral for the pregnant.

Water-soluable iron is a mineral which produces blood. It is the most significant factor for making blood and essential to produce hemoglobin conveying oxygen to all body organs. A lack of iron causes anemia, aphylaxis, headache, pale complexion, hyposexuality, etc.

Water-soluable natrium is a mineral in relation to sterilization. It controls balance of electrolyte; maintains acidity and alkalinity of body fluids; helps production of digestive fluids of stomach; and controls osmotic pressure for entering nutrient substances into blood. A lack of natrium causes heatstroke, vomiting, dyspnea and asthenia. Too much natrium causes high blood pressure, edema, stomach disorder, stomach cancer, cardiac disease, arteriosclerosis, etc.

Water-soluable magnesium is a mineral which controls mind. It calms nerves and mind and improves defensive power toward stress. It counts for about 0.02% of weight and 70% of it exists in bones and teeth. Also, water-soluable magnesium act as a catalyst in activation of enzyme and energy production. A lack of magnesium generates angiectasis, amnestic syndrome, convulsive disease, protein metabolism disorder, arrhythmia, a heart attack, etc.

*Glycyrrhiza uralensis* Fischer is a herbaceous perennial similar to beans. The root is dried in the sun and used in oriental herb medicine, effective for removing bacteria, the cause of dental caries and gum disease (Tonguibogam).

Chinese pepper is *Zanthoxylum piperitum* De Candolle or pericarp, belonging to the Rutaceae family. Used as medicine herb by removing seeds as much as possible, Chinese pepper is effective for periodontal disease and toothache (Tonguibogam).

Green tea is made from leaves that have not fermented and it is good for removing cavities and bad breath (Tonguibogam).

Belonging to the umbelliferae family, *angelica gigas* Nakai refers to traditional Chinese medicine in which the root is dried in the sun and the property of *angelica gigas* Nakai is gentle with bittersweet taste. It contains essential oil and vitamin E, and is used for the treatment of abnormal menstrual cycle, amenorrhoea, menorrhalgia, diseases related to pregnant women and fetus and all diseases after childbirth (Tonguibogam).

*Rehmannia glutinosa* var. *purpurea* is perennial herb and used for voice loss of pregnant women, heat production, heat cooling, removal of heat death of blood meal, cure for damaged body fluids, removal of extravasated blood, and insecticide (Tonguibogam).

*Sophora flavescens* Alton is a herbaceous perennial similar to beans. It is so called as 'a cane of a thief'. The reason for the calling of *Sophora flavescens* Alton is very bitter taste and the reason for the calling of 'a cane of a thief' is its ugly-bent root. *Sophora flavescens* Alton grows to 1 meter tall and is greenish, but blackish when it is young. Belonging to odd-pinnate unijugate leaves, it has alternate leaves and long leafstalks. Lightly yellow flowers come out during June to August; the ends of original stems and branches have more flowers. The roots are used in traditional medicine herbs. It contains matrine and has been revealed in animal tests that it has alleviation of fever and antidiuretic effects. Due to strong stomach function, it is good for enterogastritis, enteritidis and bacillary dysentery with taking elecampanes and *Glycyrrhiza uralensis* Fischer (Tonguibogam).

*Platycodon grandiflorum* A. De candole is an oriental herb medicine from which roots or periderms of balloonflower, belonging to campanulaceae family, and is used for sore throats, a chest cold, sputum, nasal stuffiness, asthma, bronchitis, pleurisy, headache, algor and amygdalitis. As pharmacological actions, phlegm discharges, blood sugar reduction, cholesterol reduction and skin bacteria control have been reported (Tonguibogam).

*Prunus mume* Slebold et Zuccarini is an oriental medicine herb in which an unripe fruit of Japanese apricot, belonging to the Rosaceae family, is fumigated with gas. *Prunus mume* Slebold et Zuccarini helps stop cough through the convergence of rise in lung energy, stop diarrhea, quench thirst which comes from lack of body fluids, and cure vomiting and stomachache caused by ascaris. It is also effective for digestive disorder and loss of appetite. *Prunus mume*, flower of Japanese apricot, is good for overburdened and indigested condition due to neurotic symptoms, an obstruction in throat, pyoderma, etc. As pharmacological actions, immunity boosting, anti-bacterial effect and control of cervical cancer have been reported (Tonguibogam).

Hereinafter, experimental examples of natural anti-bacterial toothpaste composition containing improvement in tooth pain, antibacterial mouth and nerve stability according to the present invention are explained as follows. The experiment was performed by Agriculture and Life Sciences Research Institute of Chungnam National University.

<Antibacterial Test>

Made up of 45% of $Na_2SiO_3$-$10H_2O$, 15% of silicon dioxide, 15% of D-sorbitol, 10% of corn starch, 4.5% of concentrated glycerin, 2.5% of *Glycyrrhiza uralensis* Fischer, 1.2% of green tea extracts, 1.2% of Chinese pepper, 0.9% of *angelica gigas* Nakai, 0.8% of *rehmannia glutinosa* rootprep, 0.6% of *Sophora flavescens* Alton, 0.6% of *Platycodon grandiflorum* A. De Candolle, 0.6% of *Prunus mume* Slebold et Zuccarini, 0.6% of calcium hydrogen phosphate dehydrate, 0.8% of peppermint oil and 0.8% of DL-menthol, the total weight of the toothpaste composition is prepared, and antibacterial activity for dangerous germs of the toothpaste composition is evaluated.

As sample strains, *Streptococcus mutans, Streptococcus Mitis, Streptococcus salivarius, Actinomyces* sp., *Neisseria* sp., *Bacteroides vulgatus, Veillonella* sp., and *Fusobacterium nucleatum* are experimented by KS K0693.

A test section and a contrast section, 0.4 g for each, are prepared; the test section is put into a glass container, capable of containing 30 ml, with a screw-driven cover; diffusion-cultured test strain (0.2 ml), selected, is inoculated to be evenly spraying on each of the test section and the contrast section in the glass container. After inoculation, they are covered and then, after 18-hour cultivation at 37±1° C., visible cell count and reduction rates of bacteria are calculated. Reduction rates of bacteria in the test section towards the contrast section are calculated by the below math formula.

$$\text{REDUCTION RATES (\%)} = \frac{(A - B)}{A} \times 100 \qquad \text{Math formula 1}$$

Here, A and B indicate the numbers of germs of the contrast section and the test section, respectively.

The results of test are shown as Table 1 below.

TABLE 1

| TYPES OF TEST BACTERIA | UNIT | TEST RESULTS CONTRAST SECTION | TEST SECTION | REDUCTION RATES (%) |
|---|---|---|---|---|
| Streptococcus mutans | cfu/g | $3.7 \times 10^6$ | $1.4 \times 10^2$ | 99.99 |
| Streptococcus mitis | cfu/g | $2.9 \times 10^6$ | $2.8 \times 10^2$ | 99.99 |
| Streptococcus salivarius | cfu/g | $2.3 \times 10^6$ | $1.1 \times 10^2$ | 99.95 |
| Actinomyces sp. | cfu/g | $4.9 \times 10^6$ | 48 | 99.99 |
| Neisseria sp. | cfu/g | $1.9 \times 10^6$ | $3.4 \times 10^2$ | 99.98 |
| Bacteroides vulgatus | cfu/g | $3.8 \times 10^6$ | $1.7 \times 10^2$ | 99.99 |
| Veillonella sp. | cfu/g | $3.2 \times 10^6$ | $1.4 \times 10^2$ | 99.99 |
| Fusobacterium nuclcatum | cfu/g | $5.8 \times 10^6$ | 98 | 99.99 |

According to periodontology in Department of Dental Science of School of Dentistry, Seoul National University, it is reported that the above 8 bacteria among dental bacteria cause dental caries and periodontal disease, the representative dental diseases, and induced diseases are shown as Table 2 below.

TABLE 2

| No | NAMES OF BACTERIA/ MICROORGANISM | INDUCED DISEASES |
|---|---|---|
| 1 | Streptococcuus mutans | DENTAL CARIES |
| 2 | Streptococcuus mitis | DENTAL CARIES, MYOENDOCARDITIS |
| 3 | Streptococcuus salivarious | DENTAL CARIES, PERIODONTAL DISEASE, BACTEREMIA, MYOENDOCARDITIS |
| 4 | Actinomyces sp. | PERIODONTAL DISEASE, LUMPY JAW, JUVENILE PERIODONTITIS |
| 5 | Neisseria sp. | PERIODONTAL DISEASE, MENINGITIS, PNEUMONIA, URETHRITIS, ARTHRITIS, HEMATOSEPSIS, SYNAPHYMENITIS |
| 6 | Bacteroides vulgatus | PERIODONTAL DISEASE, STOMATITIS, DISEASES OF DENTAL PULP OR ALVEOLAR PERIOSTEUM |
| 7 | Veillonella sp. | PERIODONTAL DISEASE, ALLERGIC RHINITIS, PROSTATITIS |
| 8 | Fusobacterium nucleatum | PERIODONTAL DISEASE, STOMATITIS |

As shown above, the toothpaste composition of the present invention enables to improve teeth by antibacterizing various kinds of dental dangerous bacteria, including *Streptococcus mutans* as representative germ causing cavities, up to 99.95%-99.99% and preventing dental caries, toothache, etc. in advance through strengthening weaken teeth and coating teeth and sealing dental tubules; to ease pain, perform preventive treatment and remove bad breath by antibacterizing (99.95%-99.99%) the total 8 bacteria, the cause of dental and gum diseases; and to stabilize nerves by silicon in water-soluable silicate and minerals, absorbed to a mouth, and stress relaxation.

<Tooth Surface Coating Test>

First, made up of 45% of $Na_2SiO_3 \cdot 10H_2O$, 15% of silicon dioxide, 15% of D-sorbitol, 10% of corn starch, 4.5% of concentrated glycerin, 2.5% of *Glycyrrhiza uralensis* Fischer, 1.2% of green tea extracts, 1.2% of Chinese pepper, 0.9% of *angelica gigas* Nakai, 0.8% of *rehmannia glutinosa* root-prep, 0.6% of *Sophora flavescens* Alton, 0.6% of *Platycodon grandiflorum* A. De Candolle, 0.6% of *Prunus mume* Slebold et Zuccarini, 0.6% of calcium hydrogen phosphate dehydrate, 0.8% of peppermint oil and 0.8% of DL-menthol, the total weight of the toothpaste composition is prepared, and coating effects of tooth surfaces of the toothpaste composition is tested.

A golden hamster is used for checking if tooth coating (film) of the tooth composition, as prepared above, is formed. A hamster has a cheek pouch for storing food in a mouth, thereby making toothpaste exposed to teeth of a hamster over a period of time by injecting toothpaste to a cheek pouch.

It is checked if there is coating (film) on tooth surfaces, extracted after 1, 2, 3 and 7 hours of injecting 1 ml of tooth composition in accordance with present invention to a cheek pouch of the golden hamster that fasted for 3 hours, by means of a scanning electron microscope (SEM).

Figure 1:
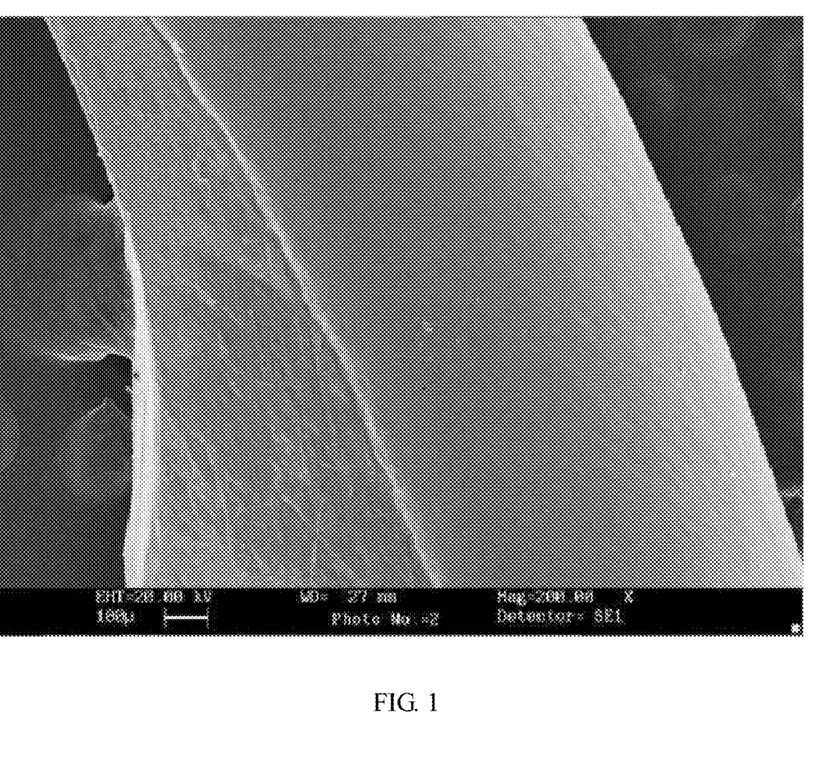
FIG. 1 is a picture(×200) showing tooth surfaces of a golden hamster that fasted for three days.

FIG. 1 is a picture (×200) showing tooth surfaces of a golden hamster that fasted for three days.

Referring to FIG. 1, it can be seen that there is no film on the tooth surfaces of the golden hamster before toothpaste treatment.

Figure 2:
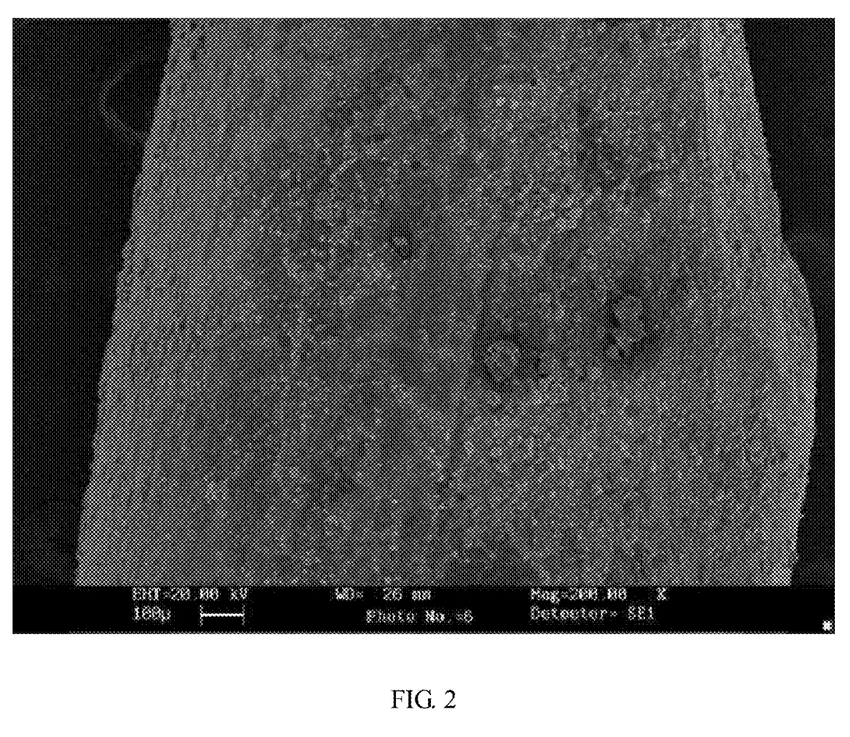
FIG. 2 is a picture(×200) showing the condition of tooth surfaces after one hour of injecting 1 ml of tooth composition in accordance with embodiment of the present invention to a cheek pouch of the golden hamster.

FIG. 2 is a picture (×200) showing the condition of tooth surfaces after one hour of injecting 1 ml of tooth composition in accordance with embodiment of the present invention to a cheek pouch of the golden hamster.

Referring to FIG. 2, it can be seen that the tooth surfaces of the golden hamster is film-coated.

Figure 3:
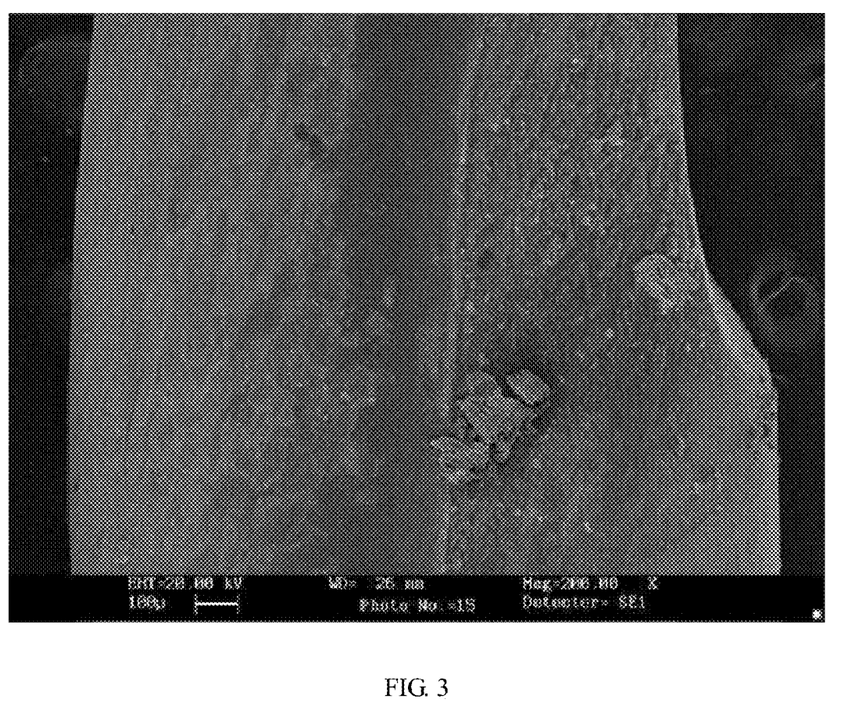
FIGS. 3 to 5 are pictures(×200) showing the conditions of tooth surfaces after 2, 3 and 7 hours, respectively, of injecting the tooth composition in accordance with the embodiment of the present invention to the cheek pouch of the golden hamster.
Figure 4:
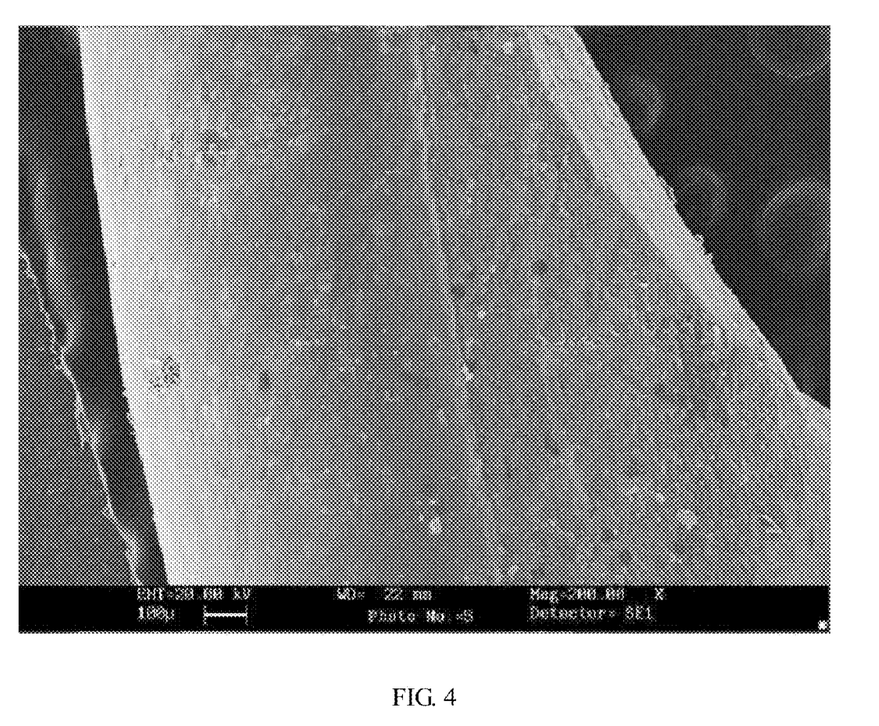
Figure 5:
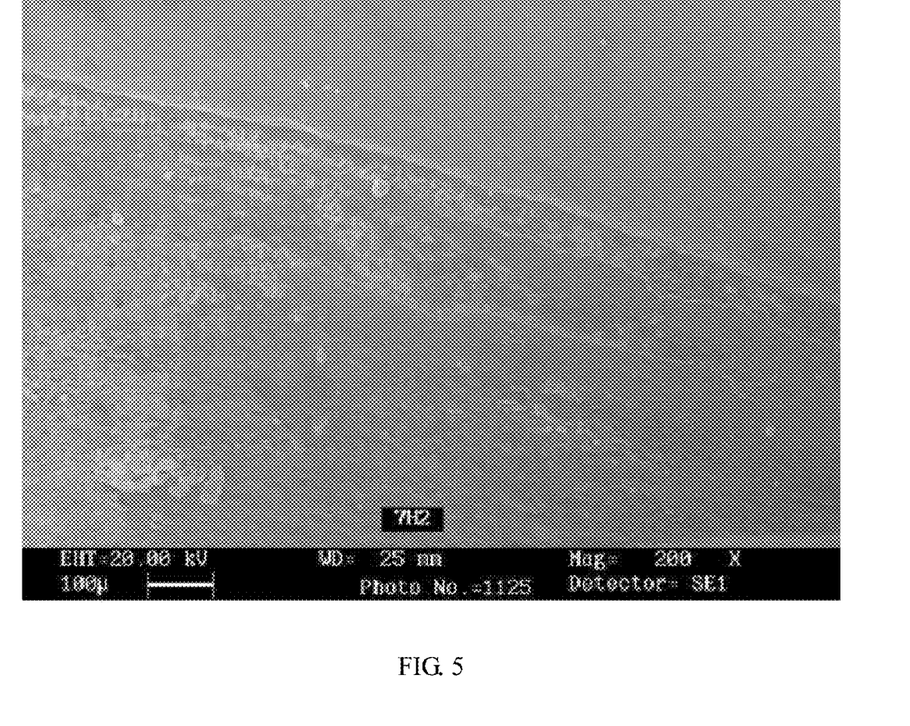

FIGS. 3 to 5 are pictures (×200) showing the conditions of tooth surfaces after 2, 3 and 7 hours, respectively, of injecting the tooth composition in accordance with the embodiment of the present invention to the cheek pouch of the golden hamster.

Referring to FIGS. 3 to 5, it can be seen that film-coating on the tooth surfaces of the golden hamster is maintained.

Next, components of tooth surfaces of a hamster after a period of time of injecting 1 ml of tooth composition in accordance with the present invention to a cheek pouch of a hamster are analyzed by an Energy dispersive X-ray analysis system (EDX).

Figure 6:
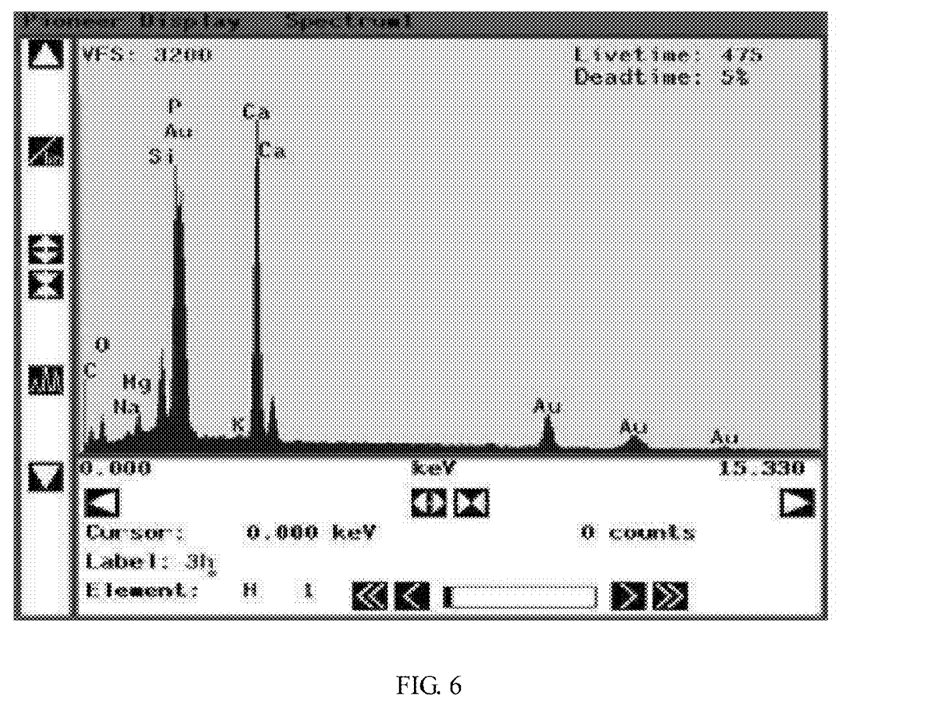
FIGS. 6 and 7 are graphs analyzing the conditions of tooth surfaces after 3 and 7 hours, respectively, of injecting the tooth composition in accordance with the embodiment of the present invention to the cheek pouch of the golden hamster, by means of a surface analysis device.
Figure 7:
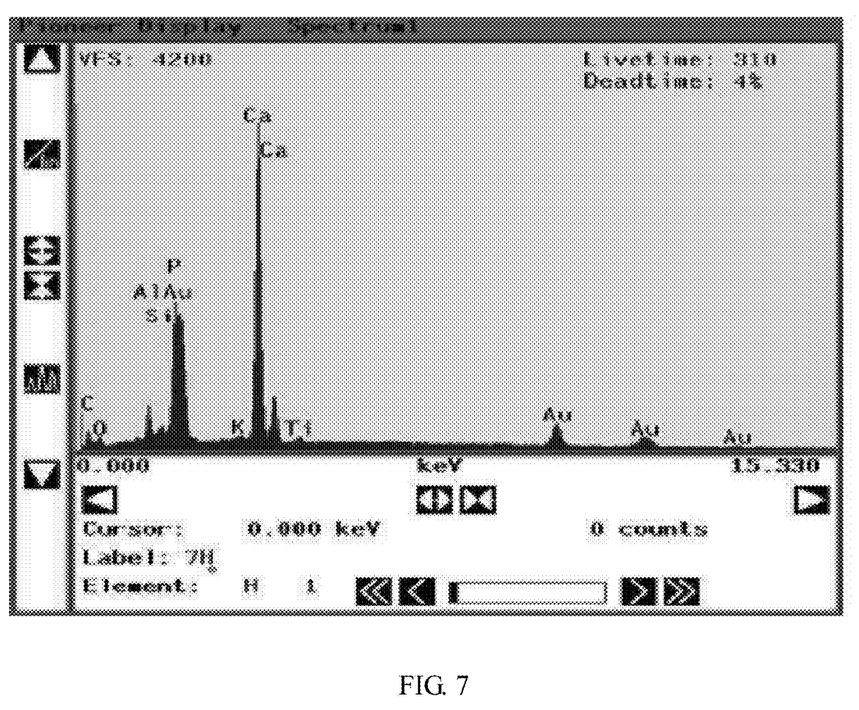

FIGS. 6 and 7 are graphs analyzing the conditions of tooth surfaces after 3 and 7 hours, respectively, of injecting the tooth composition in accordance with the embodiment of the present invention to the cheek pouch of the golden hamster, by means of the EDX.

Referring to FIGS. 6 and 7, it can be seen that there is silicon coated on the tooth surfaces.

Next, as test pretreatment, drinking water is provided for making the cheek pouch of the golden hamster empty, and the golden hamster is fed during 4 hours after 3 hours of injecting 1 ml of tooth composition to the cheek pouch of the golden hamster without 5-hour food supply. After food supply, the maintaining condition of the coating of the surface of the extracted tooth of the golden hamster is checked by an electron microscope and the component of the tooth surface is analyzed by the EDX.

Figure 8:
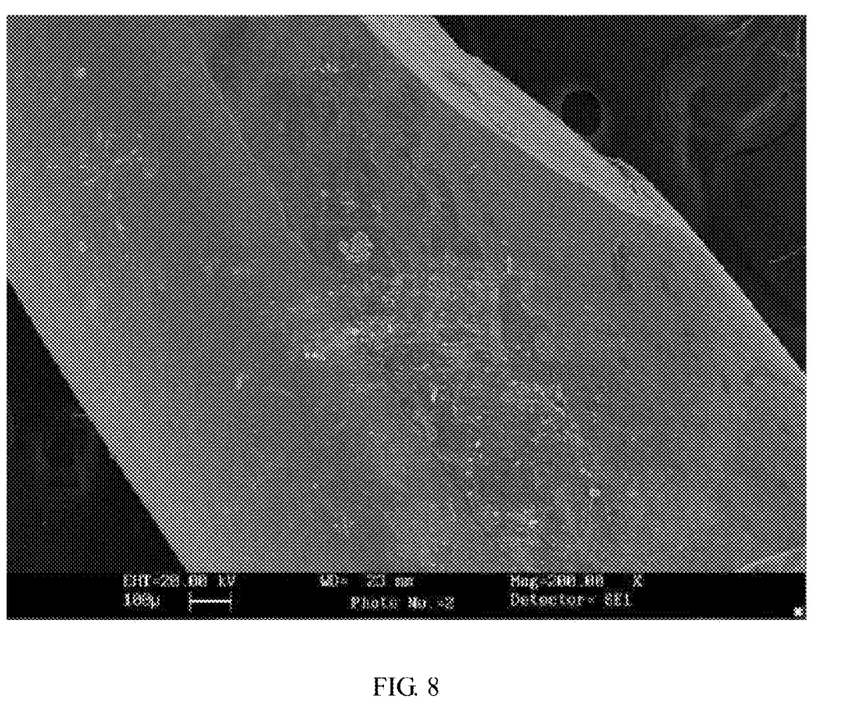
FIG. 8 is a picture showing the teeth of the golden hamster after 4-hour food supply in accordance with the embodiment of the present invention.
Figure 9:
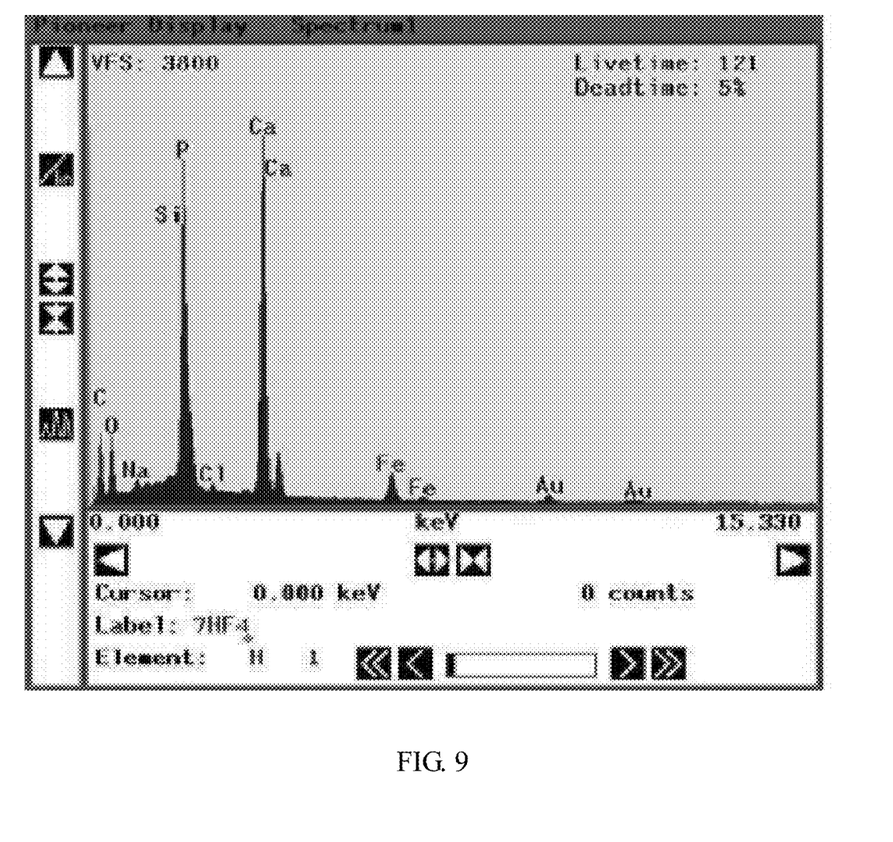
FIG. 9 is a graph showing the component analysis of the tooth surfaces of the golden hamster after 4-hour food supply in accordance with the embodiment of the present invention.

FIG. 8 is a picture showing the teeth of the golden hamster after 4-hour food supply in accordance with the embodiment of the present invention, and FIG. 9 is a graph showing the component analysis of the tooth surfaces of the golden hamster after 4-hour food supply in accordance with the embodiment of the present invention.

Referring to FIGS. 8 and 9, it can be seen that the coating of the tooth surfaces is maintained even for 4 hours after food supply, and silicon is detected from the tooth surfaces.

As a result, the tooth composition in accordance with the embodiment of the present invention enables to form films on the tooth surfaces for more than 7 hours, and films help protect teeth and soften teeth for a long time.

<Dental Tubules Sealing Test>

First, made up of 45% of $Na_2SiO_3$-$10H_2O$, 15% of silicon dioxide, 15% of D-sorbitol, 10% of corn starch, 4.5% of concentrated glycerin, 2.5% of *Glycyrrhiza uralensis* Fischer, 1.2% of green tea extracts, 1.2% of Chinese pepper, 0.9% of *angelica gigas* Nakai, 0.8% of *rehmannia glutinosa* root-prep, 0.6% of *Sophora flavescens* Alton, 0.6% of *Platycodon grandiflorum* A. De Candolle, 0.6% of *Prunus mume* Slebold et Zuccarini, 0.6% of calcium hydrogen phosphate dehydrate, 0.8% of peppermint oil and 0.8% of DL-menthol, the total weight of the toothpaste composition is prepared, and sealing effects of dental tubules of the toothpaste composition is tested.

Figure 10:
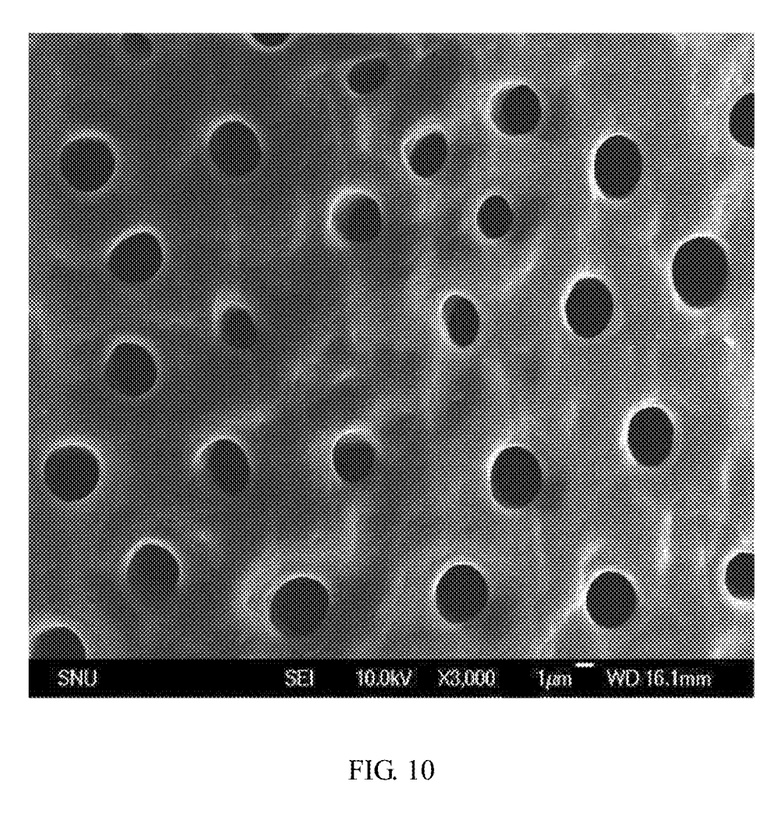
FIGS. 10 and 11 are pictures showing the condition before and after sealing dental tubules of the tooth composition in accordance with the embodiment of the present invention.
Figure 11:
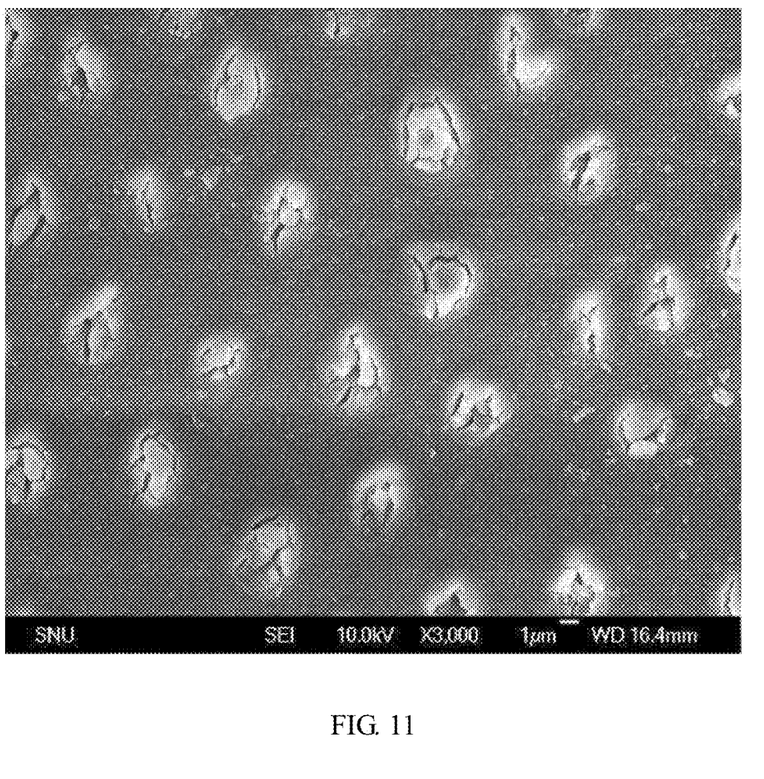

FIGS. 10 and 11 are pictures showing the condition before and after sealing dental tubules of the tooth composition in accordance with the embodiment of the present invention.

Referring to FIGS. 10 and 11, it can be seen that exposed dental tubules are sealed after three weeks of using the toothpaste of the present invention. That is, the dental tubules, the cause of toothache, are blocked and then, toothache is alleviated and prevented. Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. An anti-bacterial toothpaste composition comprising:
   24-55 wt % of $Na_2SiO_3$-$10H_2O$,
   12-25 wt % of powdered silicon dioxide,
   14-17 wt % of liquid D-sorbitol,
   8-12 wt % of powdered corn starch,
   4-5 wt % of liquid concentrated glycerin,
   2-3 wt % of liquid *Glycyrrhiza uralensis* Fischer,
   1-2 wt % of liquid Chinese pepper,
   0.4-2 wt % of liquid green tea extracts,
   0.6-1 wt % of liquid *angelica gigas* Nakai,
   0.4-1 wt % of liquid *rehmannia glutinosa* var. *purpurea*,
   0.4-1 wt % of liquid *Sophora flavescens* Alton,
   0.4-1 wt % of liquid *Platycodon grandiflorum* A. De Candolle,
   0.4-1 wt % of liquid *Prunus mume* Slebold et Zuccarini,
   0.4-1 wt % of powdered calcium hydrogen phosphate dehydrate,
   0.2-2 wt % of peppermint oil, and
   0.2-2 wt % of liquid DL-menthol.

* * * * *